United States Patent [19]

Bohn et al.

[11] Patent Number: 4,599,318

[45] Date of Patent: Jul. 8, 1986

[54] TISSUE PROTEIN $PP_{19}$, A PROCESS FOR OBTAINING IT, AND ITS USE

[75] Inventors: Hans Bohn, Marburg; Wilhelm Winckler, Wenkbach, both of Fed. Rep. of Germany

[73] Assignee: Behringwerke Aktiengesellschaft, Marburg/Lahn, Fed. Rep. of Germany

[21] Appl. No.: 699,435

[22] Filed: Feb. 7, 1985

[30] Foreign Application Priority Data

Feb. 9, 1984 [DE] Fed. Rep. of Germany ....... 3404563

[51] Int. Cl.$^4$ .................... C07K 15/14; A61K 35/42; A61K 35/50; A61K 39/395
[52] U.S. Cl. .................................. 436/543; 424/85; 424/88; 424/105; 424/95; 436/547; 435/7; 530/395; 530/414; 530/416; 530/413; 530/419; 530/417
[58] Field of Search ............. 260/112 B, 112 R; 424/85, 105, 88; 436/543, 547; 435/7

[56] References Cited

U.S. PATENT DOCUMENTS

| | | | |
|---|---|---|---|
| 4,254,021 | 3/1981 | Bohn et al. | 260/112 B |
| 4,301,064 | 11/1981 | Bohn | 260/112 R |
| 4,302,385 | 11/1981 | Bohn et al. | 260/112 B |
| 4,325,866 | 4/1982 | Bohn | 260/112 B |
| 4,368,148 | 1/1983 | Bohn | 260/112 B |
| 4,468,345 | 8/1984 | Bohn et al. | 260/112 R |
| 4,500,451 | 2/1985 | Bohn et al. | 260/112 R |
| 4,507,229 | 3/1985 | Bohn | 260/112 B |
| 4,524,027 | 6/1985 | Bohn | 260/112 R |

*Primary Examiner*—Howard E. Schain
*Attorney, Agent; or Firm*—Finnegan, Henderson, Farabow, Garrett & Dunner

[57] ABSTRACT

The protein $PP_{19}$ which has
(a) an electrophoretic mobility in the region between that of $\alpha_1$ and of $\beta_1$ globulins;
(b) an isoelectric point between 4.6 and 5.4;
(c) a sedimentation coefficient $s_{20,w}$ of $3.25 \pm 0.25$ S;
(d) a molecular weight determined in the ultracentrifuge of $36,500 \pm 4,000$;
(e) a carbohydrate fraction of $3.9 \pm 1.5$ g/100 g (mannose $0.3 \pm 0.2$, fucose $0.2 \pm 0.1$, galactose $1.0 \pm 0.3$, glucose $0.4 \pm 0.2$, N-acetylglucosamine $1.2 \pm 0.3$, N-acetylgalactosamine $0.1 \pm 0.1$, and N-acetylneuraminic acid $0.7 \pm 0.3$, each g/100 g); and
(f) a particular amino acid composition,
is described, as is a process for obtaining it.

11 Claims, 2 Drawing Figures

U.S. Patent            Jul. 8, 1986            4,599,318
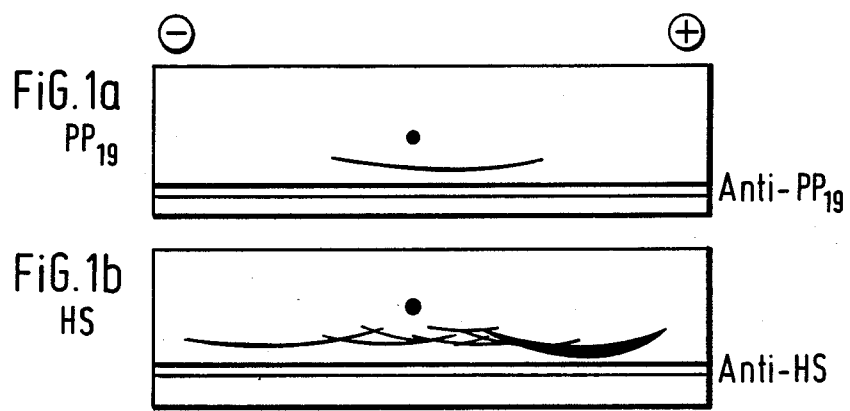

TISSUE PROTEIN PP19, A PROCESS FOR OBTAINING IT, AND ITS USE

The invention relates to a tissue protein, called $PP_{19}$, and to a process for obtaining it. $PP_{19}$ can be used to prepare antisera which can be employed for the detection and determination of $PP_{19}$ in tissue and in body fluids in order to diagnose diseases of particular organs, as a "marker" for monitoring the course of an illness or for monitoring a treatment.

Proteins are of course known in the state of the art, including tissue proteins, but none having the properties indicated below for $PP_{19}$.

The invention relates to the protein $PP_{19}$ which has the following characteristics:

(a) an electrophoretic mobility in the region between that of $\alpha_1$ and of $\beta_1$ globulins;
(b) an isoelectric point between 4.6 and 5.4;
(c) a sedimentation coefficient $s_{20,w}$ of $3.25 \pm 0.25$ S;
(d) a molecular weight determined in the ultracentrifuge of $36,500 \pm 4,000$; and
(e) a carbohydrate fraction of $3.9 \pm 1.5$ g/100 g (mannose $0.3 \pm 0.2$, fucose $0.2 \pm 0.1$, galactose $1.0 \pm 0.3$, glucose $0.4 \pm 0.2$, N-acetylglucosamine $1.2 \pm 0.3$, N-acetylgalactosamine $0.1 \pm 0.1$, and N-acetylneuraminic acid $0.7 \pm 0.3$, each g/100 g).

The aminoacid composition of $PP_{19}$ is shown in the table below:

| Amino acid | Residues per 100 residues | Coefficient of variation |
| --- | --- | --- |
| lysine | 8.63 | 2.92 |
| histidine | 1.71 | 14.20 |
| arginine | 2.73 | 7.71 |
| aspartic acid | 11.51 | 3.99 |
| threonine | 4.20 | 15.75 |
| serine | 7.48 | 2.26 |
| glutamic acid | 11.09 | 3.20 |
| proline | 4.12 | 18.29 |
| glycine | 6.88 | 5.12 |
| alanine | 7.56 | 3.30 |
| cystine ½ | 2.10 | 22.58 |
| valine | 7.44 | 3.98 |
| methionine | 2.39 | 7.24 |
| isoleucine | 3.40 | 6.38 |
| leucine | 10.03 | 7.29 |
| tyrosine | 2.19 | 2.96 |
| phenylalanine | 5.05 | 2.58 |
| tryptophan | 1.42 | 15.43 |

The following may be detailed to explain the characterizing features of the tissue protein:

The electrophoretic mobility was determined in the micro modification on cellulose acetate films (supplied by Sartorius) using sodium diethylbarbiturate buffer, pH 8.6, and a Microzone R 200 apparatus from Beckman Instruments.

The isoelectric point was measured using a column (440 ml) supplied by LKB, Stockholm. The Ampholin ® mixture had a pH range from 4.0 to 6.0.

The sedimentation coefficient was determined in an analytical ultracentrifuge supplied by Beckman (Spinco apparatus, model E) at 60,000 rpm, in double-sector cells using the UV scanner technique at 280 nm. The solvent used was water. The protein concentration was 2 g/l.

The sedimentation equilibrium method was used to determine the molecular weight in the ultracentrifuge. The concentration of the protein was adjusted to about 1.0 O.D. (optical density) for this purpose. The solvent used was a 0.05 mol/l phosphate buffer (pH 6.8) which contained 0.2 mol/l NaCl. The determination was carried out at 9,000 rpm. Recording was carried out at 280 nm using a photoelectric scanner.

The carbohydrates were determined as follows: After hydrolysis of the glycosidic bonds, the liberated neutral sugars were separated as borate complexes on an anion exchanger column (Y. C. Lee et al., Anal. Biochem. 27 (1969), 567), stained in the eluate by admixture of Cu(1) bicinchoninate reagent (K. Mopper and M. Gindler, Anal. Biochem. 56 (1973), 440) and determined quantitatively using rhamnose as the internal standard. The aminosugars were detected and determined by their reaction with ninhydrin. The neuraminic acid content was measured by the method of Warren (Methods in Enzymology, Vol. VI (1963), 463–465).

The aminoacid analysis was carried out by the method of S. Moore, D. H. Spackman, W. H. Stein, Anal. Chem. 30 (1958), 1185, using a Multichrom B liquid chromatograph supplied by Beckman. Cystine was determined as cysteic acid following oxidation of the protein with performic acid (S. Moore et al., Anal. Chem. 30 (1958), 1185) and subsequent chromatography (S. Moore, J. Biol. Chem. 238 (1963), 235). The tryptophan content was measured by direct photometric determination by the method of H. Edelhoch, Biochemistry 6 (1967), 1948.

On investigation of extracts from various human organs using immunochemical methods, $PP_{19}$ was detected in relatively high concentrations in placenta and in the stomach and in lower concentrations in the spleen. Extracts of other human organs, such as heart, lung, liver, kidney, adrenal, colon, rectum, jejunum and uterus either do not contain this protein or contain only traces of it. Proteins which are immunochemically identical or closely related to $PP_{19}$ have also been detected in extracts of monkey placentae.

Accordingly, human, as well as animal, organs in which $PP_{19}$ occurs can be used for the isolation of this protein. Mature human placentae are particularly suitable for this purpose, since they are produced in large quantities and they contain the protein in a sufficiently high concentration.

A mature human placenta contains on average about 90 mg of $PP_{19}$. Only about 75% of the $PP_{19}$ contained in the placenta dissolves on extraction of the organ with dilute salt or buffer solutions, for example with physiological NaCl solution. It appears that the rest of the protein is associated with membranes in the tissue and does not dissolve until solubilizing agents are used, for example chaotropic salt solutions or, even better, 6 mol/l urea solution or 0.5 mol/l glycine HCl buffer (pH 2.5) or ionic detergents.

Accordingly, to obtain $PP_{19}$ it is possible to use either the protein extract obtained from placentae with dilute salt solutions or the protein extract of placentae obtained, after washing out the soluble constituents, from the tissue residue by solubilization (for example with 6 mol/l urea or acid glycine buffer). The proteins obtained by the two methods are immunochemically identical and their physicochemical properties are also essentially in agreement.

$PP_{19}$ has the following properties which can be used in a process for its isolation, by employing measures appropriate for these properties:

(1) It is precipitated from aqueous solutions with ammonium sulfate at a pH of 5–8 and 30–70% saturation;

(2) It is essentially precipitated with water-soluble acridine bases, for example 2-ethoxy-6,9-diaminoacridine lactate, at a pH of 8–9 and a concentration of the base of 4 to 8 g/l. It is only partially precipitated at a pH of 6.0 and a base concentration of 4 g/l;

(3) It remains essentially in the supernatant on addition of ethanol to a solution in a physiological saline solution, or one of similar dilution, at pH 7, up to a concentration of 200 ml of alcohol per l of solution;

(4) On separation by electrophoresis, at a pH of 7–9, it is found in the region between $\alpha_1$ and $\beta_1$ globulins;

(5) On isoelectric focussing, it appears in the pH range 4.6 to 5.4;

(6) On gel filtration using Sephadex ®, it behaves like proteins having molecular weights of 20,000 to 60,000;

(7) It can be bound to weakly basic ion exchangers, for example DEAE-cellulose or DEAE-Sephadex, at a conductivity of about 0–2 mS and a pH of about 7 to 9, and can be eluted with more concentrated salt solutions (10–50 g/l NaCl solutions);

(8) It can be enriched in and isolated from an aqueous solution by immunoadsorption.

Accordingly, the invention also relates to a process for obtaining or enriching $PP_{19}$, which comprises subjecting an extract obtained, using dilute salt or buffer solutions, from organs which contain this protein to one or more of the following measures:

(a) Precipitation of the protein $PP_{19}$ with ammonium sulfate in the pH range 5 to 8 and at 30–70% saturation;

(b) Precipitation of the protein $PP_{19}$ using a water-soluble acridine base at a pH of 8 to 9 and a concentration of the base of 4–8 g/l;

(c) Separation out of part of the accompanying proteins by addition of ethanol at pH 7 up to a final concentration of 200 ml/l alcohol;

(d) Preparative zone electrophoresis, where the protein fraction between $\alpha_1$ and $\beta_1$ globulins is obtained;

(e) Gel filtration or ultrafiltration, where proteins in the molecular weight range 20,000 to 60,000 are obtained;

(f) Adsorption on to a weakly basic ion exchanger and elution of the protein $PP_{19}$;

(g) Enrichment by immunoadsorption.

The invention also relates to a process for obtaining or enriching $PP_{19}$, which comprises comminuting organs which contain this protein and washing with physiological saline solution until all the soluble constituents are removed, extracting the tissue residue with a solution of a solubilizing agent, for example a 6 mol/l urea solution or a 0.5 mol/l glycine HCl buffer (pH 2.5), and, after neutralization and thorough dialysis, subjecting the resulting extract to one or more of the measures (a) to (g) described above.

Apart from ammonium sulfate, it is also possible to use for the precipitation of $PP_{19}$ other neutral salts customarily used in preparative biochemistry. Apart from an acridine base, it is also possible to use within the scope of the process according to the invention a water-soluble derivative of a quinoline base, as are known for protein fractionations. As appropriate for its electrophoretic behavior, its charge and its molecular weight, it is also possible to apply to the isolation of the protein other measures which are suitable to separate a protein having the indicated properties from other proteins.

It is possible to use for this purpose the various methods of preparative electrophoresis, isoelectric focussing, gel filtration or ultrafiltration as well as the property of $PP_{19}$ of being able to be bound to weakly basic ion exchangers and eluted again from them.

However, the specific property of $PP_{19}$ of being able to be partially bound to membranes and eluted from them using acid glycine buffer or 6 mol/l urea solution is especially suitable for the isolation of this protein.

In particular, it is possible to isolate $PP_{19}$ by an appropriate combination of the measures mentioned, which bring about enrichment of $PP_{19}$ or separation of this protein from other proteins.

Apart from the parameters indicated, it is also possible to use immunochemical methods for the detection and determination of $PP_{19}$, for example in a fraction from a separation operation, since $PP_{19}$ has antigenic properties.

An antiserum which can be used for this purpose can be obtained as follows:

On fractionation of a placental extract with 2-ethoxy-6,9-diaminoacridine lactate and ammonium sulfate by the method of Bohn, H., (Arch.Gynakol. (1971) 210, 440), part of the $PP_{19}$ goes into placental fraction II. If this fraction is further separated by gel filtration on Sephadex G-150, then $PP_{19}$ appears in the low molecular weight protein range (molecular weights 20,000 to 60,000). A polyvalent antiserum which contains, inter alia, antibodies to $PP_{19}$ is obtained by immunization of rabbits with this fraction. This antiserum can be made essentially specific to the antigen $PP_{19}$ by absorption with normal human serum, with placental fractions which do not contain $PP_{19}$, or with particular placental proteins, such as $PP_4$.

This antiserum can be used, on the one hand, for the immunological detection of $PP_{19}$ and, on the other hand, for the preparation of an immunoadsorbent which can be employed for the enrichment and isolation of $PP_{19}$.

Monospecific antisera can be prepared, by immunization of animals by known methods, using the purified $PP_{19}$ obtained in accordance with Example 1 and, in particular, in accordance with Example 2 of the present application.

FIG. 1a shows the immunological reaction of $PP_{19}$ with a specific antiserum from rabbits, after separation in an electric field in agar-containing gels.

For comparison with this, FIG. 1b shows the separation of the proteins of the serum, visualized by their immune reaction with a rabbit antiserum to human serum (HS).

It is also possible to employ for the immunological detection of $PP_{19}$ the Ouchterlony gel diffusion technique (Schultze and Heremans, Molecular Biology of Human Proteins, Vol. 1, page 134) or, if necessary, more sensitive methods, such as radioimmunoassays or enzyme immunoassays.

The detection and determination of $PP_{19}$ have diagnostic significance. $PP_{19}$ is a tissue protein which occurs in relatively high concentration only in particular organs. When there is a disorder of these organs, as a consequence of increased cell death there can be an increase above normal in the concentration of the tissue protein $PP_{19}$ in the serum or in other body fluids, for example in the urine, of the patients. The detection and determination of $PP_{19}$ in body fluids can thus be used for the diagnosis of diseases of these organs or as a marker for monitoring the course of the illness and for monitoring the treatment.

Thus, $PP_{19}$ can be used to prepare antisera which can be employed to detect and to determine $PP_{19}$ and to construct immunochemical methods.

The invention is illustrated by the examples which follow:

EXAMPLE 1

(A) Extraction of the placentae and fractionation of the extract using an acridine base and ammonium sulfate 1,000 kg of deep-frozen human placentae were comminuted in a cutter-mixer and extracted with 1,000 l of a 4 g/l sodium chloride solution. After removal of the tissue residue by centrifugation, the extract was then adjusted to pH 6.0 with 200 ml/l acetic acid solution and, with stirring, 200 l of a 30 g/l solution of 2-ethoxy-6,9-diaminoacridine lactate (Hoechst AG) are added. The precipitate was removed by centrifugation and discarded. 10 g/l Betonit A (supplied by Erbsloh & Co., Geisenheim/Rhein) were added to the supernatant, the pH was adjusted to 7.0 by addition of 2 N NaOH, and the mixture was filtered. 300 g/l ammonium sulfate was slowly added, with stirring, to the filtrate; this resulted in the placental protein $PP_{19}$ precipitating out together with other proteins. The precipitate was filtered off. About 12 kg of a moist paste were obtained, and this is denoted fraction A below.

(B) Fractionation with ethanol 500 g of fraction A were dissolved in 400 ml of water and dialysed against physiological saline solution at 4° C. After the dialysis, the conductivity of the solution was adjusted to 15 mS by addition of a 50 g/l NaCl solution. The solution was then cooled to 0° C. and, with stirring, ethanol containing 960 g/l was added to a final concentration of the alcohol of 200 g/l. The precipitate was then removed by centrifugation. The supernatant was dialysed first against water and then against a 0.1 mol/l tris HCl buffer (pH 8.0), which contained 1 mol/l NaCl and 1 g/l $NaN_3$ (buffer solution II). The proteins were then precipitated out by addition of 380 g/l of solid ammonium sulfate. The precipitate was dissolved in water and dialysed against buffer solution II. About 850 ml of a solution (fraction B), which contained on average 140 mg of $PP_{19}$, were obtained.

(C) Enrichment of $PP_{19}$ by immunoadsorption

1. Preparation of the immunoadsorbent 340 ml of a rabbit anti-$PP_{19}$ serum were dialysed against 0.02 mol/l phosphate buffer (pH 7.0), and chromatographed on DEAE-cellulose to remove the immunoglobulins. The immunoglobulin fraction (289 g of protein) was then reacted with 289 g of specially purified agarose in the form of beads (Sepharose ® 4 B supplied by Pharmacia, Uppsala, Sweden) which had been activated with 36.2 g of cyanogen bromide, and thus was covalently bonded to a carrier. A suitable process is described by, for example, Axen et al., Nature 214, 1302 (1967). It was possible to isolate the protein $PP_{19}$ from its solution, in particular from placental fractions enriched in $PP_{19}$, using an immunoadsorbent prepared in this manner.

2. Immunoadsorption procedure

The immunoadsorbent was suspended in buffer solution II (0.1 mol/l tris HCl buffer, pH 8.0, containing 1.0 mol/l NaCl and 1 g/l $NaN_3$), and a chromatography column (5.0×20 cm) was filled with it and washed with buffer solution II. Then half the amount of fraction B was applied to the column, the $PP_{19}$ being bound by immunoadsorption. The column was thoroughly washed with buffer II. The adsorbed protein was then eluted from the column using about 600 ml of 3 mol/l potassium thiocyanate solution. The eluates containing $PP_{19}$ were dialysed against buffer solution II and concentrated to about 10 ml in an ultrafilter. Yield per adsorption about 6 mg of $PP_{19}$.

Immediately after the elution of $PP_{19}$, the adsorbent in the column was neutralized again with buffer solution I and thoroughly washed. It was then reused for the binding of $PP_{19}$ by immunoadsorption.

(D) Final purification of $PP_{19}$

The protein obtained by immunoadsorption was frequently still contaminated by non-specifically bound serum proteins and other placental proteins. Most of the other serum proteins were removed by gel filtration on Sephadex G-100. The other proteins remaining were then removed by inverse or negative immunoadsorption, that is to say using carrier-bound antibodies to the proteins which were still present as contaminants. These were essentially immunoglobulins and placental tissue proteins $PP_7$, $PP_9$, $PP_{11}$, and $PP_{13}$, as well as an erythrocyte protein, called $EP_3$.

The isolation of the placental tissue proteins $PP_7$, $PP_9$, $PP_{11}$ and $PP_{13}$ has already been described (German Offenlegungsschrift No. 2,640,387, European Patent A 0,037,963, European Patent A 0,029,191 and German Offenlegungsschrift No. 3,230,996). Antisera against these proteins have been obtained by immunization of rabbits with these proteins.

The erythrocyte protein $EP_3$ found as a contaminant in the $PP_{19}$ fraction has a considerably smaller molecular weight (about 15,000) than $PP_{19}$, and is thus already removed to a large extent from $PP_{19}$ in the gel filtration on Sephadex G-100. It appears in the low molecular weight fractions (molecular weight below 20,000), almost completely free of other proteins. Antisera against the erythrocyte protein were obtained by immunization of rabbits with this subsidiary fraction and were used for the preparation of a corresponding immunoadsorbent.

EXAMPLE 2

(A) Comminution and washing of the placentae

For the isolation of the membrane-associated fraction of $PP_{19}$, mature human placentae, as are produced at delivery, were comminuted in the frozen state using a cutter-mixer and were stored in this form at −20° C. until used. First all soluble tissue proteins were removed by washing with physiological NaCl solution. For this purpose, 700 ml of NaCl solution were added to 500 g of the comminuted placental tissue, and the mixture was briefly homogenized, then stirred at 4° C. for several hours and finally centrifuged. The supernatant was discarded, and the residue was again stirred with 700 ml of NaCl solution for several hours and centrifuged again. This washing process was repeated a total of 6 times. Soluble constituents were essentially removed from the placental tissue in this manner.

(B) Extraction of the placental tissue with Triton ® X-100

The tissue residue was extracted three times with 700 ml each time of a solution of 2 ml of polyethylene glycol p-isooctylphenyl ether (Triton ® X-100) in 100 ml of water, on each occasion being stirred at 4° C. for 20 hours and then centrifuged down. The treatment with the non-ionic detergent Triton ® X-100 served to remove the membrane-associated proteins $MP_1$ and $MP_2$ (German Offenlegungsschriften Nos. 3,314,293 and 3,334,405). Hardly any of the membrane-associated portion of protein $PP_{19}$ dissolves during this procedure.

(C) Solubilization of $PP_{19}$ with acid glycine buffer

To solubilize $PP_{19}$, the tissue residue after the treatment with Triton ® X-100 was stirred twice with 500 ml each time of a 0.5 mol/l glycine HCl buffer (pH 2.5) at 4° C. for 2 hours, and centrifuged down. The extracts were then dialysed against a 0.1 mol/l tris HCl buffer (pH 8.0) which contained 1 mol/l NaCl and 1 g/l sodium azide (buffer solution II). After the dialysis, the solutions were each concentrated to about 100 ml with an ultrafilter (supplied by Amicon) using PM-10 membranes. On average the extracts of the residues from the original 500 g of placental tissue contained a total of about 20 mg of $PP_{19}$ (fraction 2A).

(D) Enrichment of $PP_{19}$ by immunoadsorption

The immunoadsorbent was prepared, and the immunoadsorption was carried out, as described in Example 1. However, in this case the $PP_{19}$ solution obtained from the placental tissue by solubilization with glycine buffer (fraction 2A) was used for the adsorption. The absorbed protein was eluted from the column with 6 mol/l urea solution.

(E) Final purification of $PP_{19}$

In general, gel filtration on acrylamideagarose AcA 34 sufficed for the final purification of the protein obtained by immunoadsorption. Any other placental tissue proteins still present in traces were removed by inverse immunoadsorption.

We claim:

1. A protein $PP_{19}$ extracted from a source of said protein and having the following characteristics:
   (a) an electrophoretic mobility in the region between that of $\alpha_1$ and of $\beta_1$ globulins;
   (b) an isoelectric point between 4.6 and 5.4;
   (c) a sedimentation coefficient $s_{20,w}$ of $3.25 \pm 0.25$ S;
   (d) a molecular weight determined in the ultracentrifuge of $36,500 \pm 4,000$;
   (e) a carbohydrate fraction of $3.9 \pm 1.5$ g/100 g (mannose $0.3 \pm 0.2$, fucose $0.2 \pm 0.1$, galactose $1.0 \pm 0.3$, glucose $0.4 \pm 0.2$, N-acetylglucosamine $1.2 \pm 0.3$, N-acetylgalactosamine $0.1 \pm 0.1$, and N-acetylneuraminic acid $0.7 \pm 0.3$, each g/100 g); and
   (f) an amino acid composition as in the following table:

| Amino acid | Residues per 100 residues | Coefficient of variation |
|---|---|---|
| lysine | 8.63 | 2.92 |
| histidine | 1.71 | 14.20 |
| arginine | 2.73 | 7.71 |
| aspartic acid | 11.51 | 3.99 |
| threonine | 4.20 | 15.75 |
| serine | 7.48 | 2.26 |
| glutamic acid | 11.09 | 3.20 |
| proline | 4.12 | 18.29 |
| glycine | 6.88 | 5.12 |
| alanine | 7.56 | 3.30 |
| cystine ½ | 2.10 | 22.58 |
| valine | 7.44 | 3.98 |
| methionine | 2.39 | 7.24 |
| isoleucine | 3.40 | 6.38 |
| leucine | 10.03 | 7.29 |
| tyrosine | 2.19 | 2.96 |
| phenylalanine | 5.05 | 2.58 |
| tryptophan | 1.42 | 15.43 |

2. A process for obtaining or enriching $PP_{19}$ as claimed in claim 1, which comprises subjecting an extract which has been obtained, using a dilute salt or buffer solution or a solution of a solubilizing agent, from at least one organ which contains this protein $PP_{19}$ to one or more of the following measures:
   (a) Precipitation of the protein $PP_{19}$ with ammonium sulfate in the pH range of 5 to 8 and at 30–70% saturation;
   (b) Precipitation of the protein $PP_{19}$ using a water-soluble acridine base at a pH of 8 to 9 and a concentration of the base of 4–8 g/l;
   (c) Separation out of part of the accompanying proteins by addition of ethanol at pH 7 up to a final concentration of 200 ml/l alcohol;
   (d) Preparative zone electrophoresis, where the protein fraction between $\alpha_1$ and $\beta_2$ globulins is obtained;
   (e) Gel filtration or ultrafiltration where proteins in the molecular weight range of 20,000 to 60,000 are obtained;
   (f) Adsorption onto a weakly basic ion exchanger and elution of the protein $PP_{19}$; and
   (g) Enrichment by immunoadsorption, to obtain or enrich said $PP_{19}$ protein.

3. The process of claim 2, wherein said organ is selected from the group consisting of placenta, stomach and spleen, wherein said buffer solution is a glycine HCl buffer and wherein said solubilizing agent is a urea solution.

4. A process for isolating the protein $PP_{19}$ of claim 1 comprising the steps of subjecting a liquid containing said protein $PP_{19}$ to at least one known procedure for isolating proteins and, in each instance, recovering that material containing said protein $PP_{19}$.

5. The protein $PP_{19}$ of claim 1, said protein being extracted from an organ or an extract of an organ.

6. The protein $PP_{19}$ of claim 5, said protein being extracted from a placenta or an extract of a placenta.

7. The protein $PP_{19}$ of claim 6, said protein being substantially pure.

8. An antiserum to the protein $PP_{19}$ of claim 1 obtained by immunizing an animal with said protein $PP_{19}$ and recovering said antiserum.

9. A method for detecting and determining protein $PP_{19}$ comprising the step of utilizing an effective amount of the antiserum of claim 8.

10. A substantially pure protein $PP_{19}$, with the following characteristics:
   (a) an electrophoretic mobility in the region between that of $\alpha_1$ and of $\beta_1$ globulins;
   (b) an isoelectric point between 4.6 and 5.4;
   (c) a sedimentation coefficient $s_{20,w}$ of $3.25 \pm 0.25$ S;
   (d) a molecular weight determined in the ultracentrifuge of $36,500 \pm 4,000$;
   (e) a carbohydrate fraction of $3.9 \pm 1.5$ g/100 g (mannose $0.3 \pm 0.2$, fucose $0.2 \pm 0.1$, galactose $1.0 \pm 0.3$, N-acetylglucosamine $1.2 \pm 0.3$, and N-acetylneuraminic acid $0.7 \pm 0.3$, each g/100 g); and
   (f) an amino acid composition as in the following table:

| Amino acid | Residues per 100 residues | Coefficient of variation |
|---|---|---|
| lysine | 8.63 | 2.92 |
| histidine | 1.71 | 14.20 |
| arginine | 2.73 | 7.71 |
| aspartic acid | 11.51 | 3.99 |
| threonine | 4.20 | 15.75 |
| serine | 7.48 | 2.26 |

-continued

| Amino acid | Residues per 100 residues | Coefficient of variation |
| --- | --- | --- |
| glutamic acid | 11.09 | 3.20 |
| proline | 4.12 | 18.29 |
| glycine | 6.88 | 5.12 |
| alanine | 7.56 | 3.30 |
| cystine ½ | 2.10 | 22.58 |
| valine | 7.44 | 3.98 |
| methionine | 2.39 | 7.24 |
| isoleucine | 3.40 | 6.38 |
| leucine | 10.03 | 7.29 |

-continued

| Amino acid | Residues per 100 residues | Coefficient of variation |
| --- | --- | --- |
| tyrosine | 2.19 | 2.96 |
| phenylalanine | 5.05 | 2.58 |
| tryptophan | 1.42 | 15.43 |

11. A method of diagnosing or monitoring a disease or monitoring the treatment of said disease, said disease being accompanied by an increase in the concentration of protein $PP_{19}$, comprising the step of utilizing in an immunochemical method the protein $PP_{19}$ of claim 1 to achieve said intended purpose with respect to said disease.

* * * * *